US011420917B2

(12) United States Patent
Du et al.

(10) Patent No.: US 11,420,917 B2
(45) Date of Patent: Aug. 23, 2022

(54) PROCESS FOR THE MANUFACTURE OF FLUOROARYL COMPOUNDS AND DERIVATIVES

(71) Applicant: Fujian Yongjing Technology Co., Ltd., Fujian (CN)

(72) Inventors: Hongjun Du, Fujian (CN); Wenting Wu, Fujian (CN)

( * ) Notice: Subject to any disclaimer, the term of this patent is extended or adjusted under 35 U.S.C. 154(b) by 0 days.

(21) Appl. No.: 16/517,544

(22) Filed: Jul. 20, 2019

(65) Prior Publication Data
US 2020/0262770 A1 Aug. 20, 2020

(30) Foreign Application Priority Data
Feb. 15, 2019 (DE) .......................... 102019103836.7

(51) Int. Cl.
*C07C 17/20* (2006.01)
*C07C 25/02* (2006.01)
(Continued)

(52) U.S. Cl.
CPC ............ *C07C 17/206* (2013.01); *B01J 27/06* (2013.01); *C07C 25/02* (2013.01); *C07C 25/13* (2013.01); *C07C 25/18* (2013.01)

(58) Field of Classification Search
CPC .................................................. C07C 17/206
See application file for complete search history.

(56) References Cited

U.S. PATENT DOCUMENTS

| 1,180,964 A | 4/1916 | Auger |
| 5,091,580 A | 2/1992 | Pews et al. |
| (Continued) | | |

FOREIGN PATENT DOCUMENTS

| CN | 102070457 | 5/2011 |
| CN | 102627553 | 8/2012 |
| | (Continued) | |

OTHER PUBLICATIONS

Wikipedia ("Microreactor" pp. 1-2) (Year: 2020).*
(Continued)

*Primary Examiner* — Medhanit W Bahta

(57) ABSTRACT

The invention relates to a new process for the manufacture of fluoroaryl compounds and derivatives thereof, in particular of fluorobenzenes and derivatives thereof, and especially wherein said manufacture relates to an environmentally friendly production of the said compounds. Thus, the present invention overcomes the disadvantages of the prior art processes, and in a surprisingly simple and beneficial manner, and as compared to the prior art processes, in particular, the invention provides a more efficient and energy saving processes, and also provides a more environmentally friendly process, for the manufacture of nuclear fluorinated aromatics, and preferably of nuclear fluorinated fluorobenzenes. Accordingly, in one aspect of the invention, an industrially beneficial process for preparing fluorobenzenes from halobenzene precursors using HF to form hydrogen halide is provided by the present invention. A beneficial and surprisingly simple use of chlorobenzene as an industrially interesting starting material in the manufacture of fluorobenzene is provided.

9 Claims, 1 Drawing Sheet

(51) Int. Cl.
*C07C 25/13* (2006.01)
*C07C 25/18* (2006.01)
*B01J 27/06* (2006.01)

(56) References Cited

U.S. PATENT DOCUMENTS

| | | | | |
|---|---|---|---|---|
| 5,281,568 | A | * | 1/1994 | Scott ................ B01J 23/26 502/307 |
| 5,946,638 | A | | 8/1999 | Jayasuriya et al. |
| 6,087,543 | A | | 7/2000 | Subramanian |
| 6,124,511 | A | * | 9/2000 | Ohnishi ................ C07C 17/21 570/167 |
| 2005/0096489 | A1 | | 5/2005 | Dolbier et al. |
| 2011/0118513 | A1 | * | 5/2011 | Smith ................ C07C 19/08 570/153 |

FOREIGN PATENT DOCUMENTS

| | | |
|---|---|---|
| CN | 105693507 | 6/2016 |
| CN | 106008143 | 10/2016 |
| CN | 106673964 | 5/2017 |
| CN | 106699539 | 5/2017 |
| CN | 106946659 | 7/2017 |
| CN | 107129511 | 9/2017 |
| CN | 107311869 | 11/2017 |
| CN | 107325001 | 11/2017 |
| CN | 107778160 | 3/2018 |
| EP | 0510491 | 10/1992 |
| EP | 0578165 | 1/1994 |
| EP | 0635482 | 1/1995 |
| EP | 0741123 | 11/1996 |
| EP | 0781745 | 7/1997 |
| EP | 1637271 | 5/2011 |
| GB | 2275924 | 9/1994 |
| GB | 2291871 | 2/1996 |
| JP | S60237051 | 11/1985 |
| JP | S63111192 | 5/1988 |
| JP | H04124159 | 4/1992 |
| WO | WO9805610 | 2/1998 |
| WO | WO0181274 | 11/2001 |
| WO | WO0196267 | 12/2001 |
| WO | WO03053580 | 7/2003 |
| WO | WO2008073471 | 6/2008 |
| WO | WO2017192564 | 11/2017 |

OTHER PUBLICATIONS

Allgemein ("High-performance ceramic microreactors in a single piece" Apr. 27, 2007). (Year: 2007).*

Olah, G. A. et al. "Hydrogen Fluoride-Antimony(V) Fluoride" Apr. 15, 2001 (Year: 2001).*

Illespie, R. J. et al. "Superacid Solutions in Hydrogen Fluoride" J. Am. Chem. Soc. 1988, 110, 18, 6053-6057 (Year: 1988).*

* cited by examiner

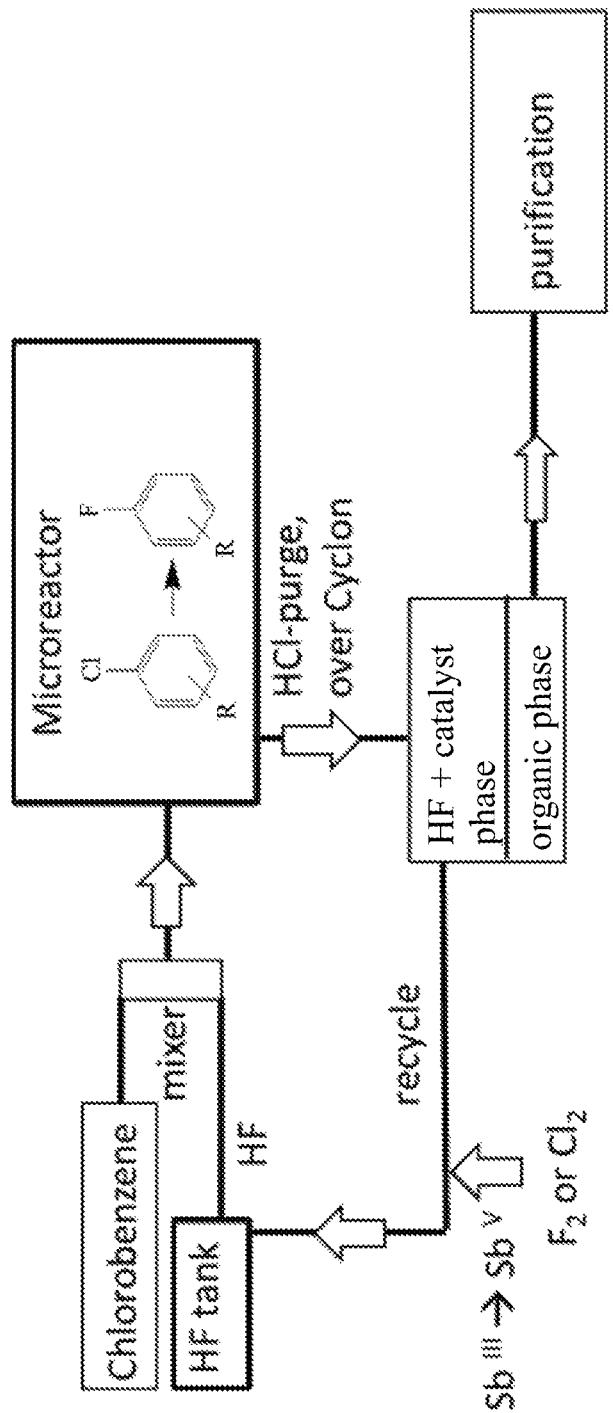

PROCESS FOR THE MANUFACTURE OF FLUOROARYL COMPOUNDS AND DERIVATIVES

BACKGROUND OF THE INVENTION

Field of the Disclosure

The invention relates to a new process for the manufacture of fluoroaryl compounds and derivatives thereof, in particular of fluorobenzenes and derivatives thereof.

Description of Related Art

All prior art processes for the manufacture of fluoroaryl compounds and derivatives thereof, today are less and less acceptable, especially in terms of environmental and work safety aspects. So far, for example and volume wise, most fluorobenzene and derivatives are industrially made with BalzSchiemann or Sandmeyer reaction, and some also with Halex reaction. These first two types of reactions are chemically working very good but disadvantageously cause a lot of waste, and also in the form of very toxic wastewater, the application of Halex reaction, especially in very large scale is limited and also causes lots of waste. For this reason, even entire chemical plants are currently closed, e.g., in China, and many companies worldwide are now without reliable and environmentally acceptable fluorobenzene sources. Same or similar problems described here by example of fluorobenzene may generally be also applicable to the preparation of other fluorinated aromatic and heteroaromatic compounds, e.g., such as used as building blocks in the pharmaceutical and agrochemical field, and for specialty polymers.

Hence, e.g., regarding fluorobenzene manufacture, there are huge problems with the waste especially from Balz-Schiemann and Sandmeyer reactions, but also from Halex reactions. For example, fluorobenzene and derivatives are important building blocks for agrochemicals, pharmaceuticals and specialty polymers and are prepared by the corresponding Balz-Schiemann reaction. Both reaction types need the production of the diazonium salt from the respective aniline step. This art of reaction especially the decomposition of tetrafluoroborate, diazonium salt, is influenced by liquefied toxic wastewater. 4 for fluoride borate 4 fluorine atoms also only 1 fluorine atom in the product used, 3 fluorine atoms go into the wastewater. For exemplary literature, without limiting, we refer to:
orgsyn.org/demo.aspx?prep=CV2P0295 and
onlinelibrary.wiley.com/doi/abs/10.1002/
cber.19270600539.

The Schiemann reaction (also called the Balz-Schiemann reaction) is a chemical reaction in which a primary aromatic amine is transformed to an aryl fluoride via a diazoniumtetrafluorofluoroborate intermediate. Both thermal and photolytic decomposition of the diazonium intermediate proceed through an arene cation, as evidenced by the equal product ratios in both cases. Named after the German chemists GüntherSchiemann and GüntherBalz, this reaction is the preferred route to fluorobenzene and some related derivatives, including 4-fluorobenzoic acid. The reaction scheme may be as follows:

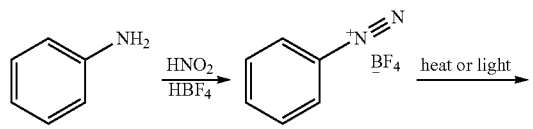

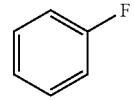

The reaction is similar to the Sandmeyer reaction, which converts diazonium salts to other aryl halides. Other Counterions have been used in place of tetrafluoroborates, such as hexafluorophosphates ($PF_6^-$) and hexafluoroantimonates ($SbF_6^-$) with improved yields for some substrates. Large-scale thermal decomposition of the diazonium salts is potentially explosive which adds another drawback for this reaction types.

The Sandmeyer reaction is a chemical reaction used to synthesize aryl halides from aryl diazonium salts. It is an example of a radical-nucleophilic aromatic substitution. The Sandmeyer reaction provides a method through which one can perform unique transformations on benzene, such as halogenation, cyanation, trifluoromethylation, and hydroxylation. The reaction scheme may be as follows:

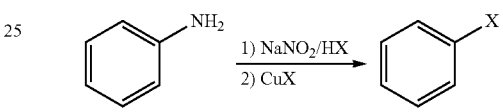

The reaction was discovered in 1884 by Swiss chemist TraugottSandmeyer, when he synthesized phenylacetylene from benzenediazonium chloride and cuprous acetylide. The reaction is a method for substitution of an aromatic amino group via preparation of its diazonium salt followed by its displacement with a nucleophile, often catalyzed by copper (I) salts. The nucleophile can include halide anions, cyanide, thiols, water, and others. The reaction does not proceed well with the fluoride anion, but fluorination can be carried out using tetrafluoroborate anions (Balz-Schiemann reaction).

The Balz-Schiemann reaction is from 1927, and in today's resource-conserving environmentally conscious time, now certainly needs a revision. Also, the sometimes alternatively considered slightly less waste-producing so-called Halex reaction works chemically only with "activated" aromatics and is industrially not or only partially suitable for fluorobenzene manufacture, but also here significant amounts of toxic waste salt are generated. Moreover, the use of expensive "F" suppliers such as AgF (for example U.S. Pat. No. 6,087,543, WO 2001/096267, WO 2008/073471, US 2005/0096489) or CsFdeclines the economy of the process. Somewhat higher yields are described in WO 2001/081274, but here again the cost-effectiveness of expensive reaction products (phosphazenes) disadvantageous in view of the relatively cheap but large-volume fluorobenzene and its derivatives.

The GB 2275924 describes the preparation of fluorobenzene from chlorobenzene in the gas phase via $CrO_3$ catalyst, but only with an unsuitable 4% industrial scale.

The JP 63111192 describes the preparation of fluorobenzene by electrofluorination. This method is energy-intensive and not sufficiently selective and therefore industrially unsuitable. In ElectrochimicaActa (1993), 38 (4), 619-24, ElectrochimicaActa (1993), 38 (8), 1123-30 and Reviews in Chemical Engineering (2003), 19 (4), 357-385 the reaction is also described.

There are many methods of producing chlorobenzene. In very early patent publications such as DE 219242 of Oct. 5, 1907, e.g., it is described the chlorination of benzene in the presence of Fe catalysts. Also, the U.S. Pat. No. 1,180,964 from Apr. 25, 1916 describes, from today's view very simple, synthesis of chlorobenzene from benzene. However, the use of chlorobenzene as an industrially interesting starting material for the very large scale manufacture of fluorobenzene is not known in the prior art.

Fluorobenzene itself serves as the starting material for many different nuclear fluorinated aromatics. For example, in the patent publication GB 2291871 the preparation of multi-nuclear fluorinated nitroaromatics with $HNO_3$ and in the presence of $F_2$ is described. Other publications in India (2002), IN 187711 A1 of Jun. 15, 2002, describe the manufacture of 2,4-dinitofluorobenzene in yields >90%.

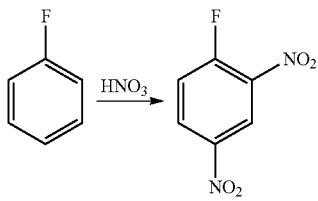

However, currently, there is no industrially suitable process for preparing fluorobenzenes from halobenzene precursors using anhydrous HF to form just hydrogen halide (which is also a sales product). Also, as said before, the use of chlorobenzene as an industrially interesting starting material for the manufacture of fluorobenzene is not known in the prior art.

The object of the present invention is to overcome the disadvantages of the prior art processes, and in particular, to provide a more efficient and energy saving processes, and also more environmentally friendly process, for the manufacture of nuclear fluorinated aromatics, and preferably of nuclear fluorinated fluorobenzenes.

SUMMARY OF THE INVENTION

In the FIGURE, shows an exemplary embodiment of a process scheme for the continuous manufacture of a fluorobenzene, or a fluorobenzene derivative, for example, also by synthesis in microreactor.

The invention relates to a new process for the manufacture of fluoroaryl compounds and derivatives thereof, in particular of fluorobenzenes and derivatives thereof, and especially wherein said manufacture, as defined in the claims and as further described herein, relates to an environmentally friendly production of the said compounds.

Thus, the present invention overcomes the disadvantages of the prior art processes, and in a surprisingly simple and beneficial manner, and as compared to the prior art processes, in particular, the invention provides a more efficient and energy saving processes, and also provides a more environmentally friendly process, for the manufacture of nuclear fluorinated aromatics, and preferably of nuclear fluorinated fluorobenzenes.

Accordingly, in one aspect of the invention, an industrially beneficial process for preparing fluorobenzenes from halobenzene precursors using HF to form hydrogen halide is provided by the present invention. In addition, the invention provides for a beneficial and surprisingly simple use of chlorobenzene as an industrially interesting starting material in the manufacture of fluorobenzene, which use of chlorobenzene was not known in the prior art before the present invention.

The Catalyst:

The processes of the invention employ a halogenation catalyst, preferably a fluorination catalyst which also can be—but not exclusively—a so called Lewis acid. Halogenation is a chemical reaction that involves the addition of one or more halogens to a compound or material. The pathway and stoichiometry of halogenation depends on the structural features and functional groups of the organic substrate, as well as on the specific halogen. Inorganic compounds such as metals also undergo halogenation. Fluorination is a halogenation wherein F (fluorine) is the halogen introduced into a compound or material. Halogenation and/or fluorination are well known to those skilled in the art, as well as the halogenation catalysts and/or fluorination catalysts involved in these reactions. For example, the addition of halogens, e.g. chlorine and/or fluorine, to alkenes proceeds via intermediate halonium ions as an active species, wherein "halonium ion" in organic chemistry denotes any onium compound (ion) containing a halogen atom, e.g. herein in context of the invention a fluorine atom, carrying a positive charge.

Halogenation catalysts and/or fluorination catalysts are well known to those skilled in the field, and preferably in context of the invention, based on Sb, As, Bi, Al, Zn, Fe, Mg, Cr, Ru, Sn, Ti, Co, Ni, preferably on the basis of Sb. More preferably a fluorination catalyst, especially an Sb fluorination catalysts providing the active species $H_2F^+SbF_6^-$, if $SbHal_5$ it is kept in an excess of HF.

For example, in one aspect of the invention, the application of antimony (Sb) catalysts for the manufacture of nuclear fluorinated aromatic systems ("fluorobenzenes") is new and advantageous. The catalyst, for example, is $SbF_5$ in HF, made naturally from $SbCl_5$. At the beginning of the reaction with fresh catalyst, of course, one or two chlorine atoms on the antimony (Sb) of the catalyst can be exchanged, and all Chlorine atoms will be exchanged after a certain time of performing the fluorination.

So far, for example, fluorobenzene and derivatives are industrially made with BalzSchiemann or Sandmeyer reaction. These two types of reactions are chemically very good but disadvantageuously cause a lot of waste, and also in the form of very toxic wastewater. For this reason, even entire chemical plants are currently closed, e.g., in China, and many companies worldwide are now without reliable and environmentally acceptable fluorobenzene sources. Same or similar problems described here by example of fluorobenzene may generally be also applicable to the preparation of other fluorinated aromatic and heteroaromatic compounds, e.g., such as used as building blocks in the pharmaceutical and agrochemical field.

The chemical novelty and concept of the invention is that a new fluorination process with use of halogenation catalysts, e.g., in preferred embodiment santimony (Sb) halides as halogenation catalysts, as used in the invention and described herein, now are provided in manufacturing processes to catalytically produce fluorobenzene and derivatives thereof, in particular without any (at least not any significant) waste by-products. The process of the invention, for example, only produces marketable hydrogen chloride (HCl) grades.

The Reactors:

In addition to the above, according to one aspect of the invention, also a plant engineering invention is provided, as used in the process invention and described herein, pertaining to the optional, and in some embodiments of the process invention, the process even preferred implementation in microreactors.

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤5 mm;

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. <1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly, just a larger volume reactor can be used and/or even several microreactors can be placed in series, optionally just having some cylinders in between for increasing residence time if necessary for completion of reaction steps. In this later case, cyclones after each microreactor help to let formed HCl to escape and to positively influence the reaction performance. Production rates can vary from milliliterspeg minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

BRIEF DESCRIPTION OF THE DRAWINGS

Aspects of the present disclosure are best understood from the following detailed description when read with the accompanying FIGURE. It is noted that, in accordance with the standard practice in the industry, various features are not drawn to scale. In fact, the dimensions of the various features may be arbitrarily increased or reduced for clarity of discussion.

The FIGURE shows an exemplary embodiment of a process scheme for the continuous manufacture of a fluorobenzene, or a fluorobenzene derivative, for example, also by synthesis in microreactor.

DESCRIPTION OF THE INVENTION

As briefly described in the Summary of the Invention, and defined in the claims and further detailed by the following description and examples herein, the invention overcomes the shortage of the state of the art that, prior to this invention, there is no industrially suitable process for preparing fluorobenzenes from halobenzene precursors using HF to form hydrogen halide.

Thus, as already mentioned, in one aspect of the invention, an industrially beneficial process for preparing fluorobenzenes from halobenzene precursors using HF to form hydrogen halide is provided by the present invention. In addition, the invention provides for a beneficial and surprisingly simple use of chlorobenzene as an industrially interesting starting material in the manufacture of fluorobenzene, which use of chlorobenzene was not known in the prior art before the present invention.

As explained supra, there is no industrially suitable process for preparing fluorobenzenes from halobenzene precursors using HF to form hydrogen halide. Since hydrogen fluoride is the first chemically utilizable stage according to the natural resource fluorspar ($CaF_2$), which is obtained from mines, and the hydrogen halide according to the invention can be further used in chemical syntheses, the catalyzed halogen-fluorine exchange on aromatics is the best environmental and process technology imaginable procedures. This is achieved by the present invention.

Antimony pentafluoride in an excess of anhydrous HF gives the superacid $H_2F^+SbF_6^-$, a strongly nucleophilic fluoride atom. It has just been found that highly fluorinated $SbF_5$ in anhydrous HF as solvent fluorinates benzenes and even deactivated halogenobenzenes in a nucleophilic exchange reaction, especially chlorobenzene, and bromobenzene and derivatives, also very deactivated precursors can be used as starting materials. This is represented by the general scheme:

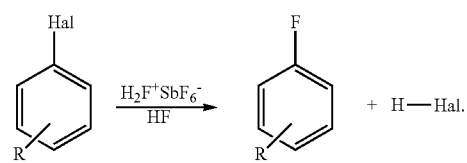

Sb-pentahalides, as such in inert solvents such as perfluorinated solvents, would function mainly as a Lewis acid and, upon hydrolysis, would provide phenols and biphenyls. Only if SbHal$_5$ undergoes a reduction to SbHal$_3$ a halogenation is possible, but not catalytically. Reactions of antimony pentafluorides with chlorobenzenes are unknown, and the skilled person would normally expect Friedel-Crafts products or just a polymerisation, decomposition or formation of undefined products and oligomers. In Journal of the Chemical Society, Perkin Transactions 2: Physical Organic Chemistry (1997) (11), 2301-2306 a reaction of chlorobenzene with phenyl disulfide is described, here SbCl$_5$ acts as a Friedel-Crafts catalyst, not as a halogenating reagent. In Theoretical and Experimental Chemistry (2011), 47 (2), 123-128, SbCl$_5$ is part of a chlorinating reagent for the scientific production of dichlorobenzene together with crown ethers and chlorine gas, but this may not be suitable as an industrial process.

However, according to the present inventions findings, if the reaction is carried out in anhydrous HF as solvent and in a temperature range starting at slightly higher temperature than ambient temperature, the nucleophilic halogen-fluorine exchange takes place in very good yields and rapid reaction rates because in (excess) HF, surprisingly, a change of functionality of the antimony pentahalide from a Friedel-Crafts catalyst function to the nucleophilic fluorination functionality, or to the fluorination agent, according to the present invention takes place, and namely in the form the super-acidic very strongly nucleophilicfluorine anion (F$^-$) which is offered to, e.g., the chlorobenzene as a reaction partner, and preferably to produce a nuclear fluorinated fluorobenzene. For example, in case of more active, the fluorination can take place already at a temperature starting from of about 40° C. But slightly higher temperatures than the said 40° C., of course, are also advantageous for bringing HCl, once formed, into the gas phase, and thereby the fluorination reaction is accelerated. Since antimony (Sb) in oxidation stage V (i.e., Sb-V) decomposes to Sb-III at a temperature starting from about 130° C., and even without any reactants being present, the upper reaction temperature should not be too high. Accordingly, in one embodiment, the temperature of the fluorination reaction is in the range of from about 40° C. to 130° C. In a preferred embodiment, the temperature of the fluorination reaction is in the range of from about 40° C. to 110° C., more preferably in the range of from about 50° C. to 110° C., even more preferably in the range of from about 60° C. to 110° C., and still more preferably in the range of from about 70° C. to 110° C. Most preferably, the temperature of the fluorination reaction is in the range of from about 80° C. to 110° C., which is the optimal temperature range. The preceding applies to all chlorobenzenes and chlorobenzene derivatives, including chlorobenzenes with chemically deactivating substituents such as other halogens or strong-pulling substituents such as cyano or nitro groups. Similarly, this applies to the manufacture other nuclear fluorinated aromatics, if such other nuclear fluorinated aromatics shall be produced from the corresponding nuclear chlorinated aromatics as the starting material. For example, but without wishing to be bound to a theory, in nucleophilic reactions, substituents such as CN and NO$_2$, which otherwise normally are deactivating, herein increase the reactivity towards nucleophiles, because electrons are attracted to the substituent, and thus the delta+ is increased at other positions and in the aromatic ring.

In the following, the general embodiments of the invention shall be described in more detail, to illustrate breadth of the invention that is duly explored and based a skilled person's educated guess, and thus derivable from the more specific embodiments described further below.

In a first embodiment, the invention relates to a process for the manufacture of fluoroaryl compounds having the following formula (I), and derivatives thereof, preferably fluorobenzenes or fluorobiphenyles, wherein the fluoroaryl compounds may substituted or unsubstituted,

RnAr—F    (I), wherein

Ar denotes a substituted or unsubstituted monocyclic homocyclic aryl or a substituted or unsubstituted homocyclic or nitrogen and/or oxygen containing heterocyclic bicyclic (—Ar—) aryl residue or a substituted or unsubstituted biaryl (—Ar—Ar'—) residue of the said monocyclic aryl and/or bicyclic (—Ar—) aryl residue, wherein Ar and Ar' may be the same or not, preferably wherein Ar is a substituted or unsubstituted phenyl (-Ph-), naphthyl or biphenyl (-Ph-Ph'—) residue, more preferably wherein Ar is a substituted or unsubstituted phenyl or biphenyl residue, Rn denotes one or more substituents selected from the group consisting of hydrogen (H), nitrogendioxide (NO2), halogen (Hal) except fluorine (F), a substituted or unsubstituted C1-C4 alkyl, a substituted or unsubstituted C1-C4 alkoxy, preferably a difluoralkoxy or trifluoralkoxy group, more preferably a difluormethoxy or trifluormethoxy group, a substituted or unsubstituted C1-C4 haloalkyl wherein the halogen (Hal) is selected from chlorine (Cl), bromine (Br) or Iodine (I), a substituted or unsubstituted C1-C4 haloalkoxy wherein the halogen (Hal) is selected from chlorine (Cl), bromine (Br) or Iodine (I), comprising the steps of:

(a) providing a starting material of formula (II)

Rn—Ar—Hal    (II);

wherein Ar and Rn have the above meaning, and Hal denotes a halogen selected from chlorine (Cl), bromine (Br) or Iodine (I);

(b) providing HF (hydrogen fluoride) and a catalyst, preferably a halogenation promoting catalyst, more preferably fluorination promoting catalyst;

(c) mixing the compound of formula (II) of (a) with the HF and the catalyst of (b);

(d) feeding the mixture obtained in (c) into at least one reactor and therein carrying out the reaction of formula (II) of (a) with the HF in the presence of the said catalyst to obtain a reaction mixture comprising the compound of formula (I);

(e) withdrawing the reaction mixture obtained in (d) from the said to yield a compound of formula (I) comprising product preferably a compound of formula (I) product; and (f) optionally purifying and/or isolating the compound of formula (I) product obtained in (e) to yield purified and/or isolated compound of formula (I).

In a second embodiment, the invention relates to a process for the manufacture, according to embodiment 1, of fluoroaryl compounds having the formula (I),

   (I), as defined in embodiment 1, and derivatives thereof, comprising the steps of:
(a) providing a starting material of formula (II),

   (II), as defined in embodiment 1;
(b) providing HF (hydrogen fluoride) and a catalyst, preferably a halogenation promoting catalyst, more preferably fluorination promoting catalyst;
(c) mixing the compound of formula (II) of (a) with the HF and the catalyst of (b);
(d) feeding the mixture obtained in (c) into at least one continuous flow reactor with upper lateral dimensions of about ≤5 mm, or of about ≤4 mm, preferably into at least one microreactor, and therein carrying out the reaction of formula (II) of (a) with the HF in the presence of the said catalyst to obtain a reaction mixture comprising the compound of formula (I);
preferably into at least one microreactor under one or more of the following conditions:
flow rate: of from about 10 ml/h up to about 400l/h;
temperature: of from about 30° C. up to about 150° C.;
pressure: of from about 4 bar up to about 50 bar;
residence time: of from about 1 second, preferably from about 1 minute, up to about 60 minutes;
(e) withdrawing the reaction mixture obtained in (d) from the said continuous flow reactor, preferably from the microreactor, to yield a compound of formula (I) comprising product preferably a compound of formula (I) product; and
(f) optionally purifying and/or isolating the compound of formula (I) product obtained in (e) to yield purified and/or isolated compound of formula (I).

In a third embodiment, the invention relates to a process for the manufacture, according to embodiment 1 or embodiment 2, of fluoroaryl compounds having the formula (I) and derivatives thereof, wherein:
(i) the fluoroaryl compound of formula (I) is a substituted or unsubstituted phenyl (-Ph-) compound having the formula (Ia), and wherein the starting material a compound of is a substituted or unsubstituted phenyl (-Ph-) compound having the formula (IIa), wherein Rn and Hal independently are as defined in embodiment 1:

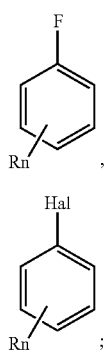

or
(ii) the fluoroaryl compound of formula (I) is a substituted or unsubstituted biphenyl (-Ph-Ph'-) compound having the formula (Ib), and wherein the starting material a compound of is a substituted or unsubstituted biphenyl (-Ph-Ph'-) compound having the formula (IIb), wherein Rn and Hal independently are as defined in embodiment 1:

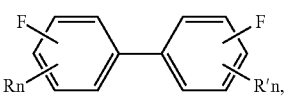   (Ib)

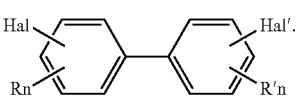   (IIb)

In a forth embodiment, the invention relates to a process for the manufacture, according to embodiment 1 or embodiment 2, of fluoroaryl compounds having the formula (I) and derivatives thereof, wherein:
(iii) the fluoroaryl compound of formula (I) is a substituted or unsubstituted phenyl (-Ph-) compound having the formula (Ic), and wherein the starting material a compound of is a substituted or unsubstituted phenyl (-Ph-) compound having the formula (IIc),

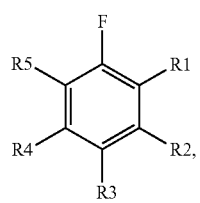   (Ic)

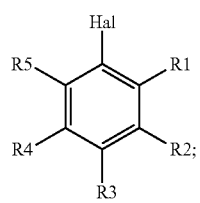   (IIc)

wherein in the formula (Ic) and in the formula (IIc):
Hal in formula (IIc) denotes a halogen selected from chlorine (Cl), bromine (Br) or Iodine (I); and
R1, R2, R3, R4, and R5 in formulae (Ic) and (IIc) independently denote a substituent selected from the group consisting of hydrogen (H), nitrogendioxide (NO2), halogen (Hal) except fluorine (F), a substituted or unsubstituted C1-C4 alkyl, a substituted or unsubstituted C1-C4 alkoxy, preferably a difluoralkoxy or trifluoralkoxy group, more preferably a difluormethoxy or trifluormethoxy group, a substituted or unsubstituted C1-C4 haloalkyl wherein the halogen (Hal) is selected from chlorine (Cl), bromine (Br) or Iodine (I), a substituted or unsubstituted C1-C4 haloalkoxy wherein the halogen (Hal) is selected from chlorine (Cl), bromine (Br) or Iodine (I); or R1, R2, and R3, in formulae (Ic) and (IIc) independently denote a substituent as defined supra, and R4 and R5 together with the carbon atom to which they are bound to the benzene ring form a substituted or unsubstituted homocyclic or nitrogen and/or oxygen containing heterocyclic 5- to 7-membered ring and system, preferably wherein R4 and R5 together represent a group selected from the group consisting of
(A) —CH=CH—CH=CH—,
(B) —CH=CH—NR6-, wherein R6 is hydrogen or C1-C4 alkyl,
(C) —CH=N—CH—,
(D) —CRxRy-O—CR'xR'y, wherein Rx, Ry, R'x, and R'y independently represent hydrogen (H), halogen (Hal) except fluorine in formula (IIc) as starting material, or fluorine or chlorine in resulting compound of formula (Ic),
preferably-CF2-O—CF2.

In a fifth embodiment, the invention relates to a process for the manufacture, according to any of embodiment 2 to 4, of fluoroaryl compounds having the formula (I) and derivatives thereof, wherein at least one of the said continuous flow reactors, preferably at least one of the microreactors, in step (d) independently is a SiC-continuous flow reactor, preferably independently is an SiC-microreactor.

In a sixth embodiment, the invention relates to a process according to any one of the embodiments 1 to 5, wherein in the fluorination reaction the catalyst is a halogenation catalyst, preferably a fluorination catalyst, on the basis of Sb, As, Bi, Al, Zn, Fe, Mg, Cr, Ru, Sn, Ti, Co, Ni, preferably on the basis of Sb, more preferably a fluorination catalyst wherein the fluorination catalyst is selected from the group consisting of Sb fluorination catalysts providing the active species $H_2F+SbF_6^-$, and including mixtures of all above mentioned catalysts. If some overfluorinationor even some polymerisation might occur by versus a given system too active catalyst or catalyst mixture, this system could be diluted by somewhat less active systems like the ones described e.g. in EP 0781745 filed in 1997. Another option for deactivations is the application of a higher SbIII content in the catalyst mixture.

In a seventh embodiment, the invention relates to a process according to embodiment 6, wherein in the fluorination reaction the halogenation catalyst is antimony pentachloride and/or antimony pentafluoride, preferably wherein the catalyst is antimony pentafluoride ($SbF_5$) and is prepared in an autoclave by reaction of $SbCl_5$ with HF, more preferably consisting of $SbF_5$ in HF which forms the active species $H_2F+SbF_6^-$, prior to reaction step (d) in the process according to any one of embodiments 1 to 5.

In a eights embodiment, the invention relates to a process according to any one of the preceding embodiments 1 to 7, wherein the process comprises in step (f) purifying and/or isolating the compound of formula (I) product obtained in (e) as defined in embodiment 1 or embodiment 2 to yield purified and/or isolated compound of formula (I).

In a ninth embodiment, the invention relates to a process according to embodiment 8, wherein in step (f) as defined in any one of embodiments 1 or 2, the purifying and/or isolating of the compound of formula (I) comprises or consists of a phase separation method.

In a tenth embodiment, the invention relates to a process according any one of the preceding embodiments 1 to 9, wherein at least in step (f) as defined in embodiment 2 for the purifying and/or isolating of the compound of formula (I) does not comprise a distillation to yield purified and/or isolated compound of formula (I).

In the following, more specific embodiments of the invention shall be described in more detail by way of example, but without being limited thereto.

Fluorobenzene serves as the starting material for many different nuclear fluorinated aromatics. As already mentioned above, in prior art the preparation of multi-nuclear fluorinated nitroaromatics with $HNO_3$ and in the presence of $F_2$ is described, as well as, e.g., the manufacture of 2,4-dinitofluorobenzene by this prior art reaction.

Of course, the synthesis sequence to 2,4-dinitrofluorobenzene can also be switched such that only the chlorobenzene is nitrated followed by chlorine/fluorine exchange by the here presented inventive method and using a strongly deactivated aromatic system such as dinitrochlorobenzene. Such a synthesis sequence is, for example, described in Japanese patent publications JP 60237051 A (1985) and JP 04124159 (1992). However, the methods described in these Japanese patent publications work with metal fluorides or in HF, and with bases as reactants of the leaving group. However, these prior art methods, if upscalable, are not catalytic, and therefore not environmentally friendly and not resource conserving. The first stage is described, for example, in Journal of the American Chemical Society (1919) 41, 1013-20, and also in more recent patent publications such as Faming ZhuanliShenqing (2011), CN102070457A. Having prepared the 2,4-dinitrochlorobenzene, then the second stage, the fluorination takes place as displayed in the reaction scheme hereunder, which is according to the present invention:

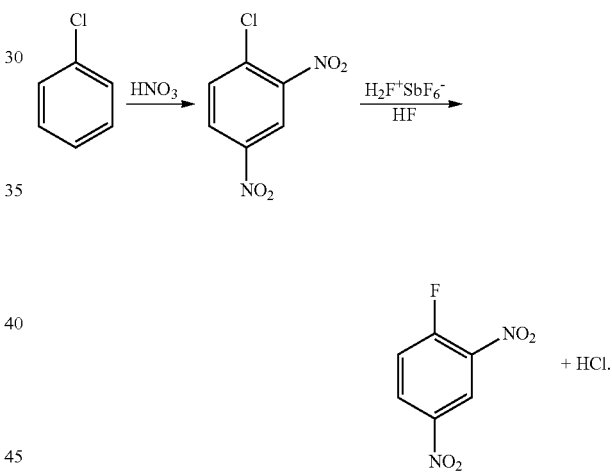

Another compound is, for example 4-fluoro-nitrobenzene which is used as a starting material, e.g., in the manufacture of active pharmaceutical ingredients such as Isavuconazole from Roche and Gefitinib from Astra Zeneca, and agroactive ingredients such as Flufenacet from Bayer Cropscience. In Faming ZhuanliShenqing (2017), CN 107129511, as prior art the fluorination of 4-chloronitrobenzene to 4-fluoronitrobenzene is described rather cumbersome in the presence of phosphorus catalysts (phase transfer conditions) and KF in DMSO in a Halex reaction, wherein large amounts of with toxic materials contaminated KClare generated and require either extensive purification, incineration or storage in an underground hazardous waste disposal facility. Again, either chlorobenzene can be selectively nitrated only in the 4-position in a first step as described in U.S. Pat. No. 5,946,638 with a yield of 96%, and thereafter as a deactivated aromatic system then can be selectively fluorinated to 4-fluoro-nitrobenzene according to the present invention, as shown in the following reaction scheme:

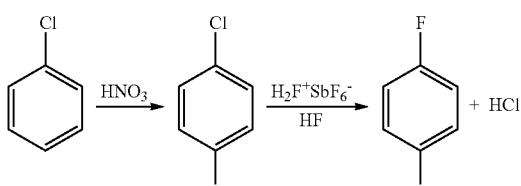

A more recent state of the art is also the production of 4-fluoronitrobenzene by decomposition of 4-nitrophenyl fluorosulfates, which must be prepared first from the corresponding phenol by reaction with $SO_2F_2$, as described in WO 2017/192564. As compared to the inventive method, this prior art procedure is not very advantageous, and cumbersome, since only 1 F-atom of 2 remains in the target molecule, and thus, larger amounts of fluoride-containing wastewater are generated. Since the corresponding F-anilines, e.g. 4-fluoroaniline are of great industrial interest, they are produced from the corresponding fluoro-nitrobenzenes, as evidenced by recent publications such as in Catalysis Letters (2018), 148 (5), 1336-1344 and Green Chemistry (2018), 20 (5), 1121-1130, by quantitative production of 4-fluoroaniline from 4-nitroaniline by reduction with hydrogen, or as described in Applied Organometallic Chemistry (2018), 32 (1) with NaBH4. Industrially, however, the reduction with Fe/HCl is usually used.

The 4-fluoroanilines find its applications, e.g., as starting material for Flumazenil from Roche, the fungicide Fluoroimide from Mitsubishi, the fungicide Bixafen from Bayer, and the herbicide Fluthiacet-methyl from FMC/Kumiai/Syngenta.

The 2,4-difluoronitrobenzene and 2,4-difluoroaniline are also of great industrial interest, and they are used, for example, in the herbicide Diflufenican from Bayer Cropscience/Adama and Difloxacin from Abbott, an animal preparation, and the herbicide Flumioxazine from Sumitomo.

The preparation, according to the present invention, e.g., the fluorination step, is carried out from the industrially available m-dichlorobenzene as follows:

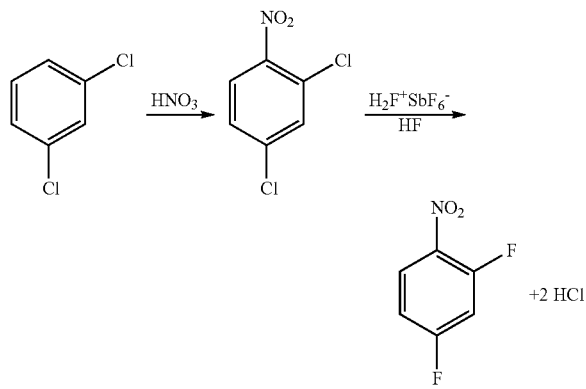

Even recent publications discuss the preparation of 2,4-difluoronitrobenzene with quantitative yields from dichloronitrobenzene, but with a non-environmentally friendly Halex reaction, as described in Catalysis Today (2012), 198 (1), 300-304, Tetrahedron (1995), 51 (22), 6363-76 and EP 635482 and WO 98/05610.

The manufacture, according to the present invention, is the fluorination in the first stage followed by the nitration:

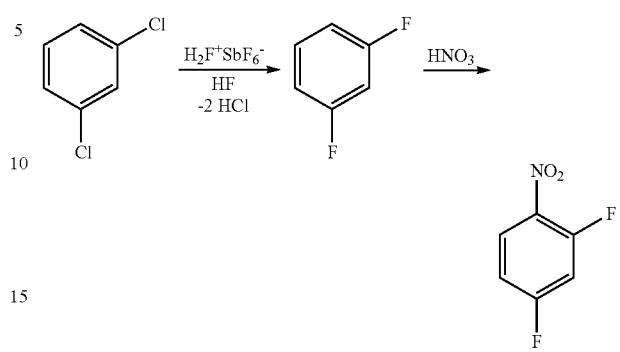

The second non-inventive step, the nitration of m-difluorobenzene, is described, for example, in Nongyao (2005), 44 (1), 13-15.

The compound 2,3,4-trifluoronitrobenzene is another very important synthetic building block in life science, especially for the so-called Floxacins (antibiotics) such as Balofloxacin from Pfizer, Elsulfavirine from Roche, and Moxifloxacin from Bayer. Recent patent publications describe the quantitative production with non-environmentally friendly Halex reaction, e.g., in Faming ZhuanliShenqing (2017), CN 107325001, and older patent publications from trihalogenonitro precursors as in EP 635482.

According to the present invention, the above non catalytic Halex reaction is performed catalytically with $SbF_5$/HF.

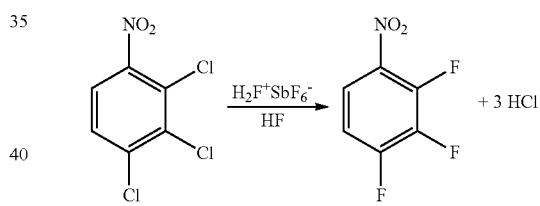

Also in CN 107325001, Guangdong Huagong (2009), 36 (3), 20-22, and also JingxiHuagongZhongjianti (2006), 36 (1), 45-46, the nitration of 1,2,3-trichlorobenzene, which here is not a reaction according to the invention, is described to produce 2,3,4-trichloronitrobenzene. A recent method for the preparation of 1,2,3-trichlorobenzene and other chlorobenzenes can be found in Faming ZhuanliShenqing (2016), CN 106008143.

Of course, according to the present invention, first the trichlorobenzene can be fluorinated and then be nitrated. Noteworthy, in the literature, by Halex reaction, only mixtures of partially fluorinated benzenes are described, however, with non-industrially suitable yields, such as e.g. in U.S. Pat. No. 5,091,580, and Journal of Fluorine Chemistry (1991). However, this prior art work did not focus on trifluorobenzene as the major product.

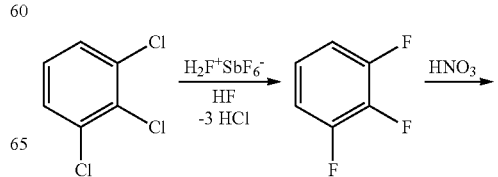

-continued

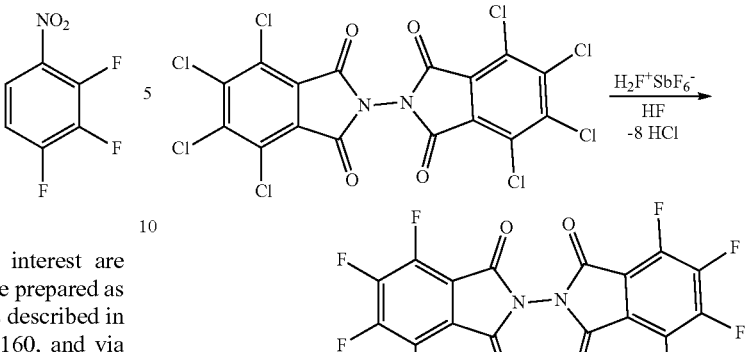

Another class of substances of particular interest are fluoroquinolones. These substances are, e.g., are prepared as starting material via tetrafluorophthalic acid, as described in Faming ZhuanliShenqing (2018), CN 107778160, and via tetrafluorophthalhydrazides in Faming ZhuanliShenqing (2016), CN 105693507, or via 2,3,4,5-tetrafluorobenzoyl chloride as described in Faming ZhuanliShenqing (2012), CN 102627553, and in an older publication via 1,1,3,3,4,5,6,7-octafluoro-1,3-dihydroisobenzofurane in Journal of Fluorine Chemistry (1988), 41 (2), 241-5. However, the preparation of all tetrafluorophthalic acid derivatives from tetrachlorophthalic acid derivatives, in turn, again requires the unfavorable, non-environmentally friendly so-called (non catalytic) Halex reaction. According to the invention, however, the fluorination is carried out with the super-acidic antimony (Sb) catalyst system, as disclosed in the claims and in this description of the invention.

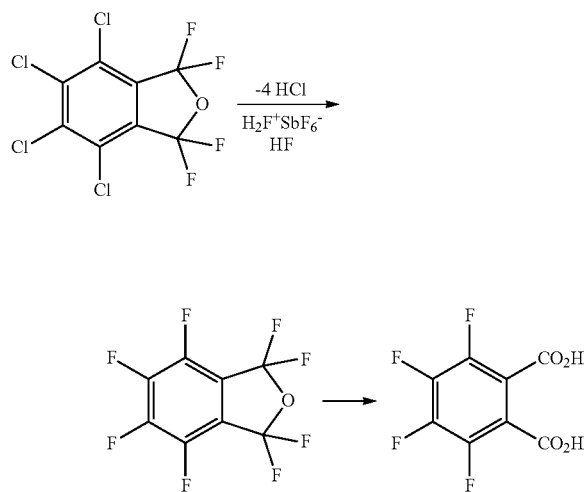

The starting material 4,5,6,7-tetrachloro-1,1,3,3-tetrafluoro-phthalan is normally prepared with expensive $SF_4$ from tetrachlorophthalic anhydride as described in Journal of Fluorine Chemistry (1987), 37 (3), 429-38. The production of tetrachlorophthalic acid is carried out according to an older patent of Höchstof 1996 (EP 741123) from N-amino-3,4,5,6-tetrachlorophthalimide, and according to EP 578165 from octafluorobisphthalimide, or as described in Faming ZhuanliShenqing (2017), CN 106699539 from tetrachlorophthalonitriles.

Also, the above namedoctafluorobisphthalimide is prepared according to EP 510491, therein Example 2, with Halex reaction with 69%, but according to the invention it is replaced by super-acidic antimony (Sb) in HF.

As also described in Faming ZhuanliShenqing (2017), CN 107311869 for the 2,3,4-trifluoronitrobenzene, the 3,4,5-nitrobenzene is also an important intermediate in Life Science, e.g., the fungicide Fluxopyroxad from BASF, and is still being produced in the prior art by Halex reaction, or as a mixture by direct fluorination/nitration as described in the already mentioned GB 2291871, or via pentafluoroaniline as described in Faming ZhuanliShenqing (2017), CN 106946659, and Faming ZhuanliShenqing (2017), CN 106673964, from pentachlorobenzonitrile, or is prepared as in Faming ZhuanliShenqing (2017), CN 106673964 by fluorination with tetrabutylammonium fluoride ($Bu_4N^+F^-$).

All reactions described can be carried out in the batch reactor or continuously in plug-flow or microreactors, as further explained in the scheme of the FIGURE, using the microreactor example. Since SbV can be reduced partially to SbIII, optionally halogen in the form of chlorine or fluorine can be fed to any HF/catalyst recycle stream downstream of the phase separator (see WO03/053580). Moreover, since the mixture of highly fluorinated antimony (Sb) catalyst with excess HF is very corrosive, according to the invention, these reactions most preferably are carried out in SiC reactors or in HDPDFE coated reactors, or in reactors that lined accordingly with SiC or HDPDFE. Also some Al coatings have positive resistance.

If the end product is a solid, the purification is preferably carried out by recrystallization. If the product is a liquid or low-melting solid, it is purified by distillation, optionally by so-called solid distillation with heated condenser.

Further Details on the Reactors:

In the use and processes according to the invention in a preferred embodiment the invention is using a microreactor. But it is to be noted in a more general embodiment of the invention, apart from the said preferred embodiment of the invention that is using a microreactor, any other, e.g. preferentially pipe-like, continuous flow reactor with upper lateral dimensions of up to about 1 cm, and as defined herein, can be employed. Thus, such a continuous flow reactor preferably with upper lateral dimensions of up to about ≤5 mm, or of about ≤4 mm, refers to a preferred embodiment of the invention, e.g. preferably to a microreactor. Continuously operated series of STRs is another option, but less preferred than using a microreactor.

In the before said embodiments of the invention, the minimal lateral dimensions of the, e.g. preferentially pipe-like, continuous flow reactor can be about >5 mm; but is usually not exceeding about 1 cm. Thus, the lateral dimensions of the, e.g. preferentially pipe-like, continuous flow reactor can be in the range of from about >5 mm up to about 1 cm, and can be of any value therein between. For example, the lateral dimensions of the, e.g. preferentially pipe-like, continuous flow reactor can be about 5.1 mm, about 5.5 mm, about 6 mm, about 6.5 mm, about 7 mm, about 7.5 mm, about 8 mm, about 8.5 mm, about 9 mm, about 9.5 mm, and about 10 mm, or can be can be of any value intermediate between the said values.

In the before said embodiments of the invention using a microreactor preferentially the minimal lateral dimensions of the microreactor can be at least about 0.25 mm, and preferably at least about 0.5 mm; but the maximum lateral dimensions of the microreactor does not exceed about ≤5 mm. Thus, the lateral dimensions of the, e.g. preferential microreactor can be in the range of from about 0.25 mm up to about ≤5 mm, and preferably from about 0.5 mm up to about ≤5 mm, and can be of any value therein between. For example, the lateral dimensions of the preferential microreactor can be about 0.25 mm, about 0.3 mm, about 0.35 mm, about 0.4 mm, about 0.45 mm, and about 5 mm, or can be can be of any value intermediate between the said values.

As stated here before in the embodiments of the invention in its broadest meaning is employing, preferentially pipe-like, continuous flow reactor with upper lateral dimensions of up to about 1 cm. Such continuous flow reactor, for example is a plug flow reactor (PFR).

The plug flow reactor (PFR), sometimes called continuous tubular reactor, CTR, or piston flow reactors, is a reactor used to perform and describe chemical reactions in continuous, flowing systems of cylindrical geometry. The PFR reactor model is used to predict the behavior of chemical reactors of such design, so that key reactor variables, such as the dimensions of the reactor, can be estimated.

Fluid going through a PFR may be modeled as flowing through the reactor as a series of infinitely thin coherent "plugs", each with a uniform composition, traveling in the axial direction of the reactor, with each plug having a different composition from the ones before and after it. The key assumption is that as a plug flows through a PFR, the fluid is perfectly mixed in the radial direction (i.e. in the lateral direction) but not in the axial direction (forwards or backwards).

Accordingly, the terms used herein to define the reactor type used in the context of the invention such like "continuous flow reactor", "plug flow reactor", "tubular reactor", "continuous flow reactor system", "plug flow reactor system", "tubular reactor system", "continuous flow system", "plug flow system", "tubular system" are synonymous to each other and interchangeably by each other.

The reactor or system may be arranged as a multitude of tubes, which may be, for example, linear, looped, meandering, circled, coiled, or combinations thereof. If coiled, for example, then the reactor or system is also called "coiled reactor" or "coiled system".

In the radial direction, i.e. in the lateral direction, such reactor or system may have an inner diameter or an inner cross-section dimension (i.e. radial dimension or lateral dimension, respectively) of up to about 1 cm. Thus, in an embodiment the lateral dimension of the reactor or system may be in the range of from about 0.25 mm up to about 1 cm, preferably of from about 0.5 mm up to about 1 cm, and more preferably of from about 1 mm up to about 1 cm.

In further embodiments the lateral dimension of the reactor or system may be in the range of from about >5 mm to about 1 cm, or of from about 5.1 mm to about 1 cm.

If the lateral dimension at maximum of up to about ≤5 mm, or of up to about ≤4 mm, then the reactor is called "microreactor". Thus, in still further microreactor embodiments the lateral dimension of the reactor or system may be in the range of from about 0.25 mm up to about ≤5 mm, preferably of from about 0.5 mm up to about ≤5 mm, and more preferably of from about 1 mm up to about ≤5 mm; or the lateral dimension of the reactor or system may be in the range of from about 0.25 mm up to about ≤4 mm, preferably of from about 0.5 mm up to about ≤4 mm, and more preferably of from about 1 mm up to about ≤4 mm.

In case reactants are solid inert solvents may be used. Thus, if raw materials shall be used, then the said solid raw materials are dissolved in an inert solvent. A suitable solvent is e.g. acetonitrile, or fully or partially fluorinated alkanes like Pentafluorobutane (365mfc), linear or cyclic partially or fully fluorinated ethers like $CF_3$—$CH_2$—$OCHF_2$(E245) or Octafluorotetrahydrofuran. Often, if available or after a first synthesis, the product as such can also serve as inert solvent.

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the the plug flow reactor and/or a tubular flow reactor, employed in this embodiment of the invention is configured with the construction materials as defined herein for the microreactors. For example, such construction materials are silicon carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

In addition to the preferred embodiments of the present invention using a microreactor according to the invention, in addition or alternatively to using a microreactor, it is also possible to employ a plug flow reactor or a tubular flow reactor, respectively.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, respectively, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic continuous flow reactor, more preferably an SiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400 l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

For example, in the embodiments of the invention the objects are achieved by a method in which at least one reaction step takes place in a microreactor. Particularly, in preferred embodiments of the invention the objects are achieved by a method in which at least one reaction step takes place in a microreactor that is comprising or is made of SiC ("SiC-microreactor"), or in a microreactor that is comprising or is made of an alloy, e.g. such as Hastelloy C, as it is each defined herein after in more detail.

Thus, without being limited to, for example, in an embodiment of the invention the microreactor suitable for, preferably for industrial, production an "SiC-microreactor" that is comprising or is made of SiC (silicon carbide; e.g. SiC as offered by Dow Corning as Type GlSiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld. Such microreactors are particularly suitable for the, preferably industrial, production of fluorinated products according to the invention.

In order to meet both the mechanical and chemical demands placed on production scale flow reactors, Plantrixmodules are fabricated from 3M™SiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 B1 and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10^{-6} K^{-1}$). Designed for flow rates ranging from 0.2 to 20 ml/min and pressures up to 25 bar, Protrix® allows the user to develop continuous flow processes at the lab-scale, later transitioning to Plantrix® MR555 (x340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarised as follows; possible reaction types are, e.g. A+B P1+Q (or C) P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300×250; number of modules/frame is one (minimum) up to four (max.). More technical information on the ChemtrixProtrix® reactor can be found in the brochure "CHEMTRIX—Scalable Flow Chemistry—Technical Information Protrix®, published by Chemtrix BV in 2017, which technical information is incorporated herein by reference in its entirety.

The Dow Corning as Type GlSiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type GlSiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type GlSiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively.

The reactor configuration of Dow Corning as Type GlSiC microreactor is characterized as multipurpose and configuration can be customized. Injection points may be added anywhere on the said reactor.

Hastelloy® C is an alloy represented by the formula NiCr21Mo14W, alternatively also known as "alloy 22" or "Hastelloy® C-22. The said alloy is well known as a highly corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0,35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur).

In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C ≤0.01%, Si ≤0.08%, Mn ≤0.05%, P ≤0.015%, S ≤0.02%. Normally, no traceable amounts of any of the following elements are found in the alloy compositions indicated above: Nb (niobium), Ti (titanium), Al (aluminum), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

In another embodiments of the invention, without being limited to, for example, the microreactor suitable for the said production, preferably for the said industrial production, is an SiC-microreactor that is comprising or is made only of SiC as the construction material (silicon carbide; e.g. SiC as offered by Dow Corning as Type GlSiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of the fluorinated products according to the invention. If more than one microreactor, preferably more than one SiC-microreactors, are used in the production, preferably in the industrial production, of the fluorinated products according to the invention, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable. Sometimes, if gaskets of a microreactor are made out of other material than HDPTFE, leakagemight occur quite soon after short time of operation because of some swelling, so HDPTFE gaskets secure long operating time of microreactor and involved other equipment parts like settler and distillation columns.

For example, an industrial flow reactor ("IFR", e.g. Plantrix® MR555) comprises of SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MRX") that affords access to A+B P type reactions. Increasing the number of modules leads to increased reaction times and/or system productivity. The addition of a quench Q/C module extends reaction types to A+B P1+Q (or C) P and a blanking plate gives two temperature zones. Herein the terms "A", "B" and "C" represent educts, "P" and "P1" products, and "Q" quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MRH" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)≤70° C.; reagent feeds of 1 to 3; maximum operating pressure (service fluid) of about 5 bar at a temperature of about 200° C.; maximum operating pressure (process fluid) of about 25 bar at a temperature of about ≤200° C.

Further Details of the Fluorination Process of the Invention:

The processes of the invention employ a halogenation catalyst, preferably a fluorination catalyst. Halogenation is a chemical reaction that involves the addition of one or more halogens to a compound or material. The pathway and stoichiometry of halogenation depends on the structural features and functional groups of the organic substrate, as well as on the specific halogen. Inorganic compounds such as metals also undergo halogenation. Fluorination is a halogenation wherein F (fluorine) is the halogen introduced into a compound or material. Halogenation and/or fluorination are well known to those skilled in the art, as well as the halogenation catalysts and/or fluorination catalysts involved in these reactions. For example, the addition of halogens, e.g. chlorine and/or fluorine, to alkenes proceeds via intermediate halonium ions as an active species, wherein "halonium ion" in organic chemistry denotes any onium compound (ion) containing a halogen atom, e.g. herein in context of the invention a fluorine atom, carrying a positive charge.

Halogenation catalysts and/or fluorination catalysts are well known to those skilled in the field, and preferably in context of the invention, based on Sb, As, Bi, Al, Zn, Fe, Mg, Cr, Ru, Sn, Ti, Co, Ni, preferably on the basis of Sb. More preferably a fluorination catalyst, especially an Sb fluorination catalysts providing the active species $H_2F^+SbF_6^-$.

In one embodiment, the invention relates to a fluorination process for the manufacture of the fluorinated products according to the invention, wherein at least one of the said continuous flow reactors, preferably at least one of the microreactors, independently is a SiC-continuous flow reactor, preferably independently is an SiC-microreactor.

In another embodiment, the invention relates to a fluorination process according to any one of the embodiments described herein, related to the manufacture of the fluorinated products according to the invention, wherein the catalyst is a halogenation catalyst, preferably a fluorination catalyst, on the basis of Sb, As, Bi, Al, Zn, Fe, Mg, Cr, Ru, Sn, Ti, Co, Ni, preferably on the basis of Sb, more preferably a fluorination catalyst wherein the fluorination catalyst is selected from the group consisting of Sb fluorination catalysts providing the active species $H_2F^+SbF_6^-$.

In yet another embodiment, the invention relates to a fluorination process according to any one of the embodiments described herein, related to the manufacture of the fluorinated products according to the invention, wherein the halogenation catalyst is antimony pentachloride and/or antimony pentafluoride, preferably wherein the catalyst is antimony pentafluoride ($SbF_5$) and is prepared in an autoclave by reaction of $SbCl_5$ with HF, more preferably consisting of $SbF_5$ in high molar excess of HF which forms the active species $H_2F^+SbF_6^-$, prior to fluorination reaction step in the process according to any one of embodiments described herein, related to the manufacture of the fluorinated products according to the invention.

In a further embodiment, the invention relates to a fluorination process according to any one of the preceding embodiments described herein, related to the manufacture of the fluorinated products according to the invention, wherein the process comprises purifying and/or isolating the fluorinated product obtained to yield purified and/or isolated fluorinated products according to the invention.

In yet a further embodiment, the invention relates to a fluorination process according to any one of the preceding embodiments described herein, related to the manufacture of the fluorinated products according to the invention, wherein the purifying and/or isolating of the fluorinated product comprises or consists of a phase separation method.

In still a further embodiment, the invention relates to a fluorination process according to any one of the preceding embodiments described herein, related to the manufacture of the fluorinated products according to the invention, wherein the purifying and/or isolating does not comprise a distillation to yield purified and/or isolated fluorinated products according to the invention.

Further Details of the Reactors Used in the Invention:

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤5 mm, or of about ≤4 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. ≤1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly and/or a larger volume reactor used. Production rates can vary from milliliters minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤5 mm, or of about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤5 mm, or of about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the the plug flow reactor and/or a tubular flow reactor, employed in this embodiment of the invention is configured with the construction materials as defined herein for the microreactors. For example, such construction materials are silicon carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic or high grade stainless steel (Inox or Hastelloy) continuous flow reactor, more preferably an SiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400 l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

Thus, without being limited to, for example, in an embodiment of the invention the microreactor suitable for, preferably for industrial, production an "SiC-microreactor" that is comprising or is made of SiC (silicon carbide; e.g. SiC as offered by Dow Corning as Type G1SiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld.

In order to meet both the mechanical and chemical demands placed on production scale flow reactors, Plantrixmodules are fabricated from 3M™SiC (Grade C). Produced using the patented 3M (EP 1 637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M® silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 B1 and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10^{-6} K^{-1}$). Designed for flow rates ranging from 0.2 to 20 ml/min and pressures up to 25 bar, Protrix® allows the user to develop continuous flow processes at the lab-scale, later transitioning to Plantrix® MR555 (x340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarised as follows; possible reaction types are, e.g. A+B P1+Q (or C) P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300×250; number of modules/frame is one (minimum) up to four (max.). More technical information on the ChemtrixProtrix® reactor can be found in the brochure "CHEMTRIX—Scalable Flow Chemistry—Technical Information Protrix®, published by Chemtrix BV in 2017, which technical information is incorporated herein by reference in its entirety.

The Dow Corning as Type G1SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type G1SiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively. The reactor configuration of Dow Corning as Type G1SiC microreactor is characterized as multipurpose and configuration can be customized. Injection points may be added anywhere on the said reactor.

Hastelloy® C is an alloy represented by the formula NiCr21Mo14W, alternatively also known as "alloy 22" or "Hastelloy® C-22. The said alloy is well known as a highly corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0,35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C ≤0.01%, Si ≤0.08%, Mn ≤0.05%, P ≤0.015%, S ≤0.02%. Normally, no traceable amounts of any of the following elements are found in the alloy compositions indicated above: Nb (niobium), Ti (titanium), Al (aluminum), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.). In another embodiments of the invention, without being limited to, for example, the microreactor suitable for the said production, preferably for the said industrial production, is an SiC-microreactor that is comprising or is made only of SiC as the construction material (silicon carbide; e.g. SiC as offered by Dow Corning as Type GISiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of the targeted compounds described herein in the context of the invention. If more than one microreactor, preferably more than one SiC-microreactors, are used in the production, preferably in the industrial production, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable.

For example, an industrial flow reactor ("IFR", e.g. Plantrix® MR555) comprises of SiC modules (e.g. 3M® SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MRX") that affords access to A+B→P type reactions. Increasing the number of modules leads to increased reaction times and/or system productivity. The addition of a quench Q/C module extends reaction types to A+B→P1+Q (or C)→P and a blanking plate gives two temperature zones. Herein the terms "A", "B" and "C" represent educts, "P" and "P1" products, and "Q" quencher.

Typical dimensions of an industrial flow reactor ("IFR", e.g. Plantrix® MR555) are, for example: channel dimensions in (mm) of 4×4 ("MRX", mixer) and 5×5 (MRH-I/MRH-II; "MRH" denotes residence module); module dimensions (width×height) of 200 mm×555 mm; frame dimensions (width×height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)≤70° C.; reagent feeds of 1 to 3; maximum operating pressure (service fluid) of about 5 bar at a temperature of about 200° C.; maximum operating pressure (process fluid) of about 25 bar at a temperature of about ≤200° C.

The following examples are intended to further illustrate the invention without limiting its scope.

EXAMPLES

Example 1

Production of Fluorobenzene from Chlorobenzene in the Batch Reactor (Autoclave)

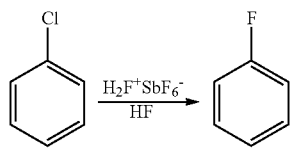

Pre-Fluorination of the Catalyst:

In a 250 ml autoclave from Roth with an inner lining made of HDPTFE, 36.78 g (0.123 mol) of $SbCl_5$ were initially charged, and then it is loaded with 20-times the molar excess of anhydrous HF (2.46 mol, 49.22 g), and the reaction mixture is maintained at 100° C. for a period of 3 h. By this procedure, about 95% of the chlorine atoms bound to the antimony was exchanged by fluorine atoms, and thus, approximately 26.7 g (0.123 mol) of $SbF_5$ are contained in the autoclave as the catalyst.

Reaction with Chlorobenzene:

After cooling down, the pressure in the autoclave is released to ambient pressure, and the autoclave containing the pre-fluorinated catalyst is again charged with 49.22 g (2.46 mol) of HF taken from 1 kg HF pressure cylinder that is charged with nitrogen ($N_2$). Subsequently, 27.69 g (0.246 mol) of chlorobenzene are slowly pressed into the autoclave by means of an HPLC-pump (HPLC=High-Pressure-Liquid-Chromatography), and an exothermic reaction and a pressure increase can be observed. Subsequently, the internal temperature of the autoclave is still heated to 60° C. for a period of 3 h, and then, after cooling down the obtained reaction mixture and relieving the autoclave pressure, the entire reaction mixture is worked-up by cautious hydrolysis. An organic phase is formed which is containing 97% of the desired fluorobenzene, and which organic phase after drying and fine distillation yields pure fluorobenzene.

Example 2

Continuous Production of Fluorobenzene in Amicroreactor

The reaction scheme for this procedure using a microreactor is shown in the FIGURE. In the continuous production of fluorobenzene in a microreactor according to this Example 2, an SiC-microreactor was employed.

First, batch-wise 500 g (2.31 mol) of $SbF_5$ were prepared by the method as described in Example 1 starting from $SbCl_5$. These 500 g of $SbF_5$ were added to the HF-tank along with 462.23 g (23.1 mol) of anhydrous HF in a setup as in the reaction scheme displayed in the FIGURE. The microreactor employed was a Chemtrixmicroreactor type Protrix made of SiC, and it had a volume of 27 ml.

Caution: Hastelloy and stainless steel microreactors such as stainless steel 1.7571 cannot be used because they corrode at the latest after 1 h of operation. Also, corrosion reduces the nucleophilicity of the catalyst (strong deactivation by forming SbIII), and thus, the rate of reaction is also reduced.

Another storage tank is filled with chlorobenzene. A pressure holding valve set to 10 bar is provided on the cyclone for an HCl-purge (as need arises during prolonged operation). Subsequently, before the starting the fluorination reaction, the SiC-microreactor is tempered to 60° C.

Then, first the dosing of the HF/catalyst mixture with a volume of 100 ml/h is started, followed by the dosing of chlorobenzene at 100 ml/h (ratio substrate to HF about 1:5.7).

The reaction mixture leaving the SiC-microreactor was passed into a phase separator having a volume of 2 l, and phase separation into HF/catalyst phase, and organic phase separation takes place. The organic phase was taken from the reaction system, and for analysis it was expanded into a NaOH-scrubber for residual fluoride removal. The GC-analysis (GC=Gas Chromatography) of the organic phase of the scrubber showed fluorobenzene with a 98% yield, and some traces of difluorobiphenyl. In more long-lasting continuous operation, the HF/catalyst phase, depending on the particular SbIII-content, is replaced with a little halogen for regeneration, and then returned to the HF-tank. Fresh HF is fed into the HF-tank during the continuous operation, in accordance with the amount of fluorobenzene formation and the removal via the organic phase (and possibly replacement of the HF entrained by the HCl via the HCl-purge).

Example 3

Production of 4-fluoronitrobenzene (Autoclave)

The experiment is repeated as described under Example 1, using 4-chloronitrobenzene as starting material instead of chlorobenzene. The yield of 4-fluoronitrobenzene was 97%.

Example 4

Production of 2,4-difluoronitrobenzene (Autoclave)

The experiment is repeated as described under Example 1, using 2,4-dinitrochlorobenzene as starting material instead of chlorobenzene. The yield of 2,4-difluoronitrobenzene was 96%.

Example 5

Production of 2,4-difluoronitrobenzene (Autoclave)

The experiment is repeated as described under Example 1, using the same amount of HF/catalyst, but only with 23.62 g (0.123 mol) of 2,4-dichloronitrobenzene as starting material instead of chlorobenzene. The yield of 2,4-difluoronitrobenzene was 98%.

Example 6

Production of 1,3-difluorobenzene (Autoclave)

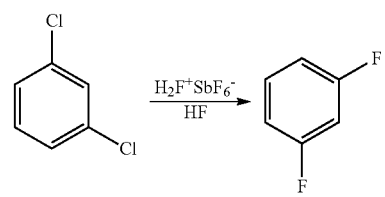

The strong nucleophilicity of the super-acidic $SbF_5$ in HF is particularly evident in view of electron-deficient systems such as dichlorobenzenes, e.g., such as m-dichlorobenzene. The preparation of the pre-fluorinated catalyst is carried out analogously to Example 1 in a autoclave batch procedure. Thereafter, after cooling down, the pressure in the autoclave is released to ambient pressure, and the autoclave containing the pre-fluorinated catalyst is again charged with 49.22 g (2.46 mol) of HF taken from 1 kg HF pressure cylinder that is charged with nitrogen (N₂). Subsequently, 27.69 g (0.246 mol) of chlorobenzene are slowly pressed into the autoclave by means of an HPLC-pump (HPLC=High-Pressure-Liquid-Chromatography), and an exothermic reaction and a pressure increase can be observed. Subsequently, 18.1 g (0.123 mol) of m-dichlorochlorobenzene are slowly pressed into the autoclave by means of an HPLC-pump (HPLC=High-Pressure-Liquid-Chromatography), and an exothermic reaction and a pressure increase can be observed. Subsequently, the internal temperature of the autoclave is still heated to 60° C. for a period of 3 h, and then, after cooling down the obtained reaction mixture and relieving the autoclave pressure, the entire reaction mixture is worked-up by cautious hydrolysis. An organic phase is formed which is containing 97% of the desired 1,3-difluorobenzene, and which organic phase after drying and fine distillation yields pure 1,3-difluorobenzene.

Example 7

Production of 1,4-difluorobenzene (Autoclave)

As described in Example 6, the procedure was repeated, but with 1,4-dichlorobenzene as starting material. The yield of the product 1,4-difluorobenzene was 95%.

Example 8

Production of Trifluoronitrobenzene (Autoclave) A still lower electron yield system, as compared to the above ones, is the trichloronitrobenzene as a starting material for the fluorination reaction according to the invention.

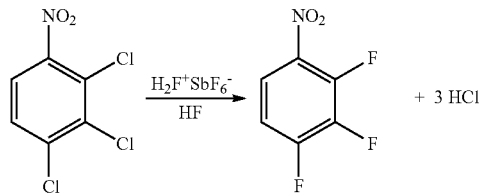

Again, the reaction is carried out analogously to Example 1, resulting in a 93% yield of trifluoronitrobenzene.

Examples 9 to 14

Continuous Production in a Microreactor

The experiments of the Examples 3-8 were carried out continuously in a microreactor analogously to the procedure of Example 2. Per each halogen atom to be exchanged, the reaction is performed analogously to Example 2, but the amount of HF was doubled.

If the raw material (starting material) to be used was a solid, prior to the reaction, the solid starting material was taken up in a little HF to allow a liquid metering thereof.

Halogenobenzenes are soluble in anhydrous HF without reaction.

It is to be noted that benzotrihalides (e.g., trichlorotoluene) would already react with HF even without a catalyst.

Thus, in Example 8, the compound is metered with a dosing of 100 ml/h of the trichloronitrobenzene (starting material) and a dosing of 300 ml/h of the HF(+catalyst). In case of possibly incomplete reaction, the residence time, which has been reduced by relative increase in the HF-dosing, can be increased again as required by a percentage reduction of both dosings, the trichloronitrobenzene-dosing and the HF(+ catalyst)-dosing.

The yields in the microreactor procedure each were 2-8% higher than in the autoclave.

What is claimed is:

1. A process for the manufacture of fluoroaryl compounds having the following formula (I), wherein the fluoroaryl compounds may be substituted or unsubstituted, $$Rn-Ar-F \quad (I),$$

wherein

Ar is a substituted or unsubstituted phenyl or biphenyl group,

Rn denotes one or more substituents selected from the group consisting of hydrogen (H), nitrogen dioxide (NO₂), halogen (Hal) except fluorine (F), a substituted or unsubstituted C1-C4 alkyl, a substituted or unsubstituted C1-C4 alkoxy, a substituted or unsubstituted C1-C4 haloalkyl and a substituted or unsubstituted C1-C4 haloalkoxy wherein the halogen (Hal) is selected from the group consisting of chlorine (Cl), bromine (Br) and Iodine (I), comprising the steps of:

(a) providing a starting material of formula (II)

$$Rn-Ar-Hal \quad (II);$$

wherein Ar and Rn have the above meaning, and Hal denotes a halogen selected from the group consisting of chlorine (Cl), bromine (Br) and Iodine (I);

(b) providing anhydrous HF (hydrogen fluoride) as a solvent and a catalyst, and the catalyst is Sb fluorination catalyst providing the active species $H_2F^+SbF_6^-$;

(c) mixing the compound of formula (II) of (a) with the HF and the catalyst of (b);

(d) feeding the mixture obtained in (c) into at least one reactor and therein carrying out the reaction of formula (II) of (a) with the HF in the presence of the said catalyst to obtain a reaction mixture comprising the compound of formula (I);

(e) withdrawing the reaction mixture obtained in (d) from the said a compound of formula (I) product; and (f) purifying and/or isolating the compound of formula (I) product obtained in (e) to yield purified and/or isolated compound of formula (I);

wherein the reactor is a microreactor and the reaction is carried out in the presence of anhydrous HF as the solvent;

wherein in the step (d) for feeding the mixture obtained in (c) into the microreactor under a plurality of following conditions:

flow rate: of from about 10 ml/h up to about 400 l/h;

temperature: of from about 30° C. up to about 150° C.;

pressure: of from about 5 bar up to about 50 bar; and residence time: of from about 1 minute, up to about 60 minutes.

2. The process according to claim 1, for the manufacture of fluoroaryl compounds having the formula (I), wherein:

(iii) the fluoroaryl compound of formula (I) is a substituted or unsubstituted phenyl (-Ph-) compound having the formula (Ic), and wherein the starting material is a substituted or unsubstituted phenyl (-Ph-) compound having the formula (IIc),

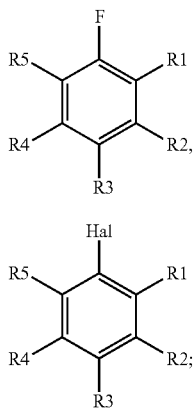

wherein in the formula (Ic) and in the formula (IIc):
Hal in formula (IIc) denotes a halogen selected from the group consisting of chlorine (Cl), bromine (Br) and Iodine (I); and
R1, R2, R3, R4, and R5 in formulae (Ic) and (IIc) independently denote a substituent selected from the group consisting of hydrogen (H), nitrogen dioxide ($NO_2$), halogen (Hal) except fluorine (F), a substituted or unsubstituted C1-C4 alkyl, a substituted or unsubstituted C1-C4 alkoxy, a substituted or unsubstituted C1-C4 haloalkyl wherein the halogen (Hal) is selected from the group consisting of chlorine (Cl), bromine (Br) and Iodine (I), and a substituted or unsubstituted C1-C4 haloalkoxy wherein the halogen (Hal) is selected from the group consisting of chlorine (Cl), bromine (Br) and Iodine (I); or R1, R2, and R3, in formulae (Ic) and (IIc) independently denote a substituent as defined supra, and R4 and R5 together with the carbon atom to which they are bound to the benzene ring form a substituted or unsubstituted homocyclic or nitrogen and/or oxygen containing heterocyclic 5- to 7-membered ring and system.

3. The process according to claim 1, for the manufacture of fluoroaryl compounds having the formula (I), wherein the microreactor a SiC-microreactor.

4. The process according to claim 1, wherein in step (f), the purifying and/or isolating of the compound of formula (I) product comprises or consists of a phase separation method.

5. The process according to claim 1, wherein in step (f) for the purifying and/or isolating of the compound of formula (I) does not comprise a distillation to yield purified and/or isolated compound of formula (I).

6. The process according to claim 1, wherein the fluoroaryl compounds having the following formula (I) is fluorobenzene.

7. The process according to claim 2, wherein R4 and R5 together represent a group selected from the group consisting of
(A) —CH=CH—CH=CH—,
(B) —CH=CH—NR6-, wherein R6 is hydrogen or C1-C4 alkyl,
(C) —CH=N—CH—, and
(D) —CRxRy-O—CR'xR'y, wherein Rx, Ry, R'x, and R'y independently represent hydrogen (H), halogen (Hal) except fluorine in formula (IIc) as starting material, or fluorine or chlorine in resulting compound of formula (Ic).

8. The process of claim 1, wherein the substituted C1-C4 alkoxy in Rn is a difluoralkoxy or trifluoralkoxy group.

9. The process of claim 1, wherein the substituted C1-C4 alkoxy in Rn is a difluormethoxy or trifluormethoxy group.

* * * * *